United States Patent
Thompson

(10) Patent No.: US 8,801,431 B2
(45) Date of Patent: Aug. 12, 2014

(54) COMBINATION TOOL FOR ANATOMICAL MEASUREMENT FOR DENTURE MANUFACTURE

(75) Inventor: Timothy C. Thompson, Fountain Hills, AZ (US)

(73) Assignee: Global Dental Science LLC, Scottsdale, AZ (US)

( * ) Notice: Subject to any disclaimer, the term of this patent is extended or adjusted under 35 U.S.C. 154(b) by 0 days.

(21) Appl. No.: 13/249,210

(22) Filed: Sep. 29, 2011

(65) Prior Publication Data

US 2013/0280672 A1  Oct. 24, 2013

Related U.S. Application Data

(60) Provisional application No. 61/409,914, filed on Nov. 3, 2010.

(51) Int. Cl.
- *A61C 9/00* (2006.01)
- *A61C 19/04* (2006.01)
- *A61C 13/00* (2006.01)

(52) U.S. Cl.
CPC ........... *A61C 9/0006* (2013.01); *A61C 13/0003* (2013.01); *A61C 19/04* (2013.01)
USPC .................. 433/42; 433/44; 433/68; 433/72; 433/214

(58) Field of Classification Search
USPC ........... 433/37, 42–46, 54–57, 68–69, 72–73, 433/199.1, 213–214; 33/513–514; 600/590, 600/587
See application file for complete search history.

(56) References Cited

U.S. PATENT DOCUMENTS

| | | | | |
|---|---|---|---|---|
| 1,652,910 A * | 12/1927 | Psayla | ............................. | 433/41 |
| 2,994,957 A * | 8/1961 | McLeod | .......................... | 433/69 |
| 4,299,573 A | 11/1981 | Ricci | | |
| 4,591,341 A | 5/1986 | Andrews | | |
| 4,634,377 A * | 1/1987 | Behrend | .......................... | 433/73 |
| 5,151,044 A | 9/1992 | Rotsaert | | |
| 5,188,529 A * | 2/1993 | Luth | ............................... | 433/68 |
| 5,672,305 A | 9/1997 | Kogure | | |
| 6,422,864 B1 * | 7/2002 | Glatt | ............................... | 433/68 |
| 6,488,503 B1 | 12/2002 | Lichkus et al. | | |

(Continued)

FOREIGN PATENT DOCUMENTS

| | | |
|---|---|---|
| JP | 2008307281 | 12/2008 |
| WO | 2009105661 | 8/2009 |

(Continued)

OTHER PUBLICATIONS

PCT; International Search Report and Written Opinion dated Jul. 18, 2012 in Application No. PCT/US2011/059230.

(Continued)

*Primary Examiner* — Heidi M Eide
(74) *Attorney, Agent, or Firm* — Snell & Wilmer L.L.P.

(57) ABSTRACT

A combination tool for defining and measuring anatomical features of a patient for the fabrication of dentures. The tool includes components for preparing a double arch impression, for determining the vertical spacing of the patient's mouth, for measuring the lip, mid line and smile lines of the patient, and for determining the occlusal plane of the patient. This single tool replaces the need for a multitude of tools typically used in preparing for the fabrication of dentures.

8 Claims, 15 Drawing Sheets

(56) References Cited

U.S. PATENT DOCUMENTS

| | | |
|---|---|---|
| 7,758,345 B1 | 7/2010 | Christensen |
| 8,641,938 B2 | 2/2014 | Howe |
| 2002/0180760 A1 | 12/2002 | Rubbert et al. |
| 2005/0175957 A1 | 8/2005 | Haje |
| 2005/0186539 A1 | 8/2005 | McLean et al. |
| 2006/0040232 A1* | 2/2006 | Shoup .................. 433/72 |
| 2006/0040236 A1 | 2/2006 | Schmitt |
| 2006/0210945 A1 | 9/2006 | Savic et al. |
| 2008/0206710 A1 | 8/2008 | Kruth et al. |
| 2009/0287332 A1 | 11/2009 | Adusumilli et al. |
| 2009/0325125 A1 | 12/2009 | Diangelo et al. |
| 2010/0086186 A1 | 4/2010 | Zug et al. |
| 2010/0094446 A1 | 4/2010 | Baloch et al. |
| 2011/0244417 A1* | 10/2011 | Hilsen et al. ............... 433/75 |
| 2013/0209962 A1 | 8/2013 | Thompson et al. |
| 2013/0216978 A1 | 8/2013 | Thompson et al. |
| 2013/0218532 A1 | 8/2013 | Thompson et al. |
| 2013/0249132 A1 | 9/2013 | Thompson et al. |

FOREIGN PATENT DOCUMENTS

| | | |
|---|---|---|
| WO | 2010022479 | 3/2010 |
| WO | 2012061652 | 5/2012 |
| WO | 2012061655 | 5/2012 |
| WO | 2012061659 | 5/2012 |
| WO | 2012061660 | 5/2012 |

OTHER PUBLICATIONS

PCT; International Preliminary Report on Patentability dated May 8, 2013 in Application No. PCT/US2011/059230.

PCT; International Search Report and Written Opinion dated Jul. 18, 2012 in Application No. PCT/US2011/059235.

PCT; International Preliminary Report on Patentability dated May 8, 2013 in Application No. PCT/US2011/059235.

PCT; International Search Report and Written Opinion dated Jul. 9, 2012 in Application No. PCT/US2011/059239.

PCT; International Preliminary Report on Patentability dated May 8, 2013 in Application No. PCT/US2011/059239.

PCT; International Search Report and Written Opinion dated Jul. 18, 2012 in Application No. PCT/US2011/059240.

PCT; International Preliminary Report on Patentability dated May 8, 2013 in Application No. PCT/US2011/059240.

EPO; European Search Report dated Mar. 4, 2014 in Application No. 11838839.6.

* cited by examiner

COMBINATION TOOL FOR ANATOMICAL MEASUREMENT FOR DENTURE MANUFACTURE

RELATED APPLICATIONS

This patent claims the benefit of provisional application 61/409,914, filed on Nov. 3, 2010.

FIELD OF THE INVENTION

This invention relates to the field of dental measurement tools and in particular, tools for measuring anatomical features for the fabrication and fitting of dentures.

BACKGROUND OF THE INVENTION

The manufacture of dentures normally require the measurement of several anatomical features of the patient in order to fabricate a denture that will properly fit and function. These measurements are normally sent to a dental lab that uses these measurements to create The dentist obtains data regarding several anatomical features of the patient to send to the dental lab. First, the dentist obtains a scan of the bite impressions. This can be done by using an upper bite impression tray, a lower bite impression tray or a triple bite impression tray that simultaneously takes both upper and lower bite impressions.

The dentist also takes additional measurements of anatomical features of the patient. These include, without limitation, the vertical height relation to the upper and lower bite alignment; the lip support of the patient; canine position; the smile line of the patient; the centric relationship of the patient; and the mid-line measurement. Other measurements may be taken as well.

The lip line measurement is intended to provide a measurement of the upper lip from the anterior papilla at rest. This is traditionally measured by a papillameter which consist of a vestibule shield, incisive papilla rest and an vertical handle with measurement increments.

The smile line measurement can also be determined by the papillameter. The device is inserted into position and the patient is requested to smile so that the lip line at that position from the anterior papilla can be measured.

The mid-line is determined from typically from the existing intraoral anatomic structures, usually the maxillary anterior (labial) frenum.

The vertical height dimension is typically determined from measurements taken from nose and chin reference points. Measurements of the vertical height are taken at rest and of the vertical dimension of occlusion.

A centric tray or bite rim is commonly used to take a double arch registration to record vertical and centric jaw registration.

The occlusal plane is an orientation of the position of an imaginary occlusal plane which theoretically touches the incisal edges of the incisors and tips of the occluding surface of the posterior teeth. A normal occlusal plane extends parallel to a line drawn from the tragus of the ear to the ala of the nose and parallel to the interpupillary line (Camper's Line). This ensures that the patient will not dislodge the lower denture, particularly while eating and not bite the lateral borders of the tongue. Tools for measuring the occlusal plane typically include a thin flat plane have a curved bite piece and a pair of laterally and distally extending wings projecting from the bite piece.

There are individual tools for each of these measurements. These include a papillameter, a centric tray, bite rim, a vertical height caliper, bite trays and other tools. This requires the practitioner to maintain a variety of different tools and be trained for each.

SUMMARY OF THE INVENTION

The present invention provides a single tool that can take most if not all of the necessary measurements for the preparation of dentures and other dental orthosis. The tool enables a variety of measurements to be obtained without the need of numerous tools in the preparation of dentures and other dental orthosis. This enables the examination of the patient to be taken in a much shorter time frame and with less discomfort to the patient. It also improves the quality of the measurements since they are taken from a single base line measurement with one tool.

The tool of a preferred embodiment includes an upper impression tray and a lower impression tray. This enables a double arch impression to be taken in a single measurement. The trays can be inserted and removed with the use of a removable handle that can be attached when needed, and removed when not to allow other measurements to be taken. A vertical adjustment mechanism allows the spacing between the upper and lower trays to be precisely adjusted. This allows the vertical spacing to be precisely measured.

The preferred embodiment of the tool also includes a removable lip support that is attached to one or both of the upper and lower trays. The lip support can include a horizontal adjustment so that the spacing between the lip support and the trays can be adjusted to allow the smile and lip lines of the patient to be accurately determined and measured. A measurement grid can be formed on the lip support so these measurements can be precisely determined. The lip support can also include an attachment mechanism for templates so the size, shape and coloring of the teeth can be matched. In one embodiment, protuberances or other devices can be attached to the lip support so that anatomical features of the patient can be simulated, such as the canine structure.

The tool of the preferred embodiment also includes a occlusal plane plate component that can be attached to the lip support, one or both of the trays, or any combination thereof. The occlusal plane plate includes a horizontal member that will be in the same plane as the tool in the patient's mouth and a pivotal member that can be pivoted to determine the occlusal plane of the patient. A calibrated scale provides the angle measured between these two members.

In use, the tool can be used to define and measure the critical anatomical features of the patient so that dentures and other orthosis can be precisely fabricated. The tool is able to form double arch dental impressions, determine the vertical spacing between the upper and lower arches, determine the lip, mid line and smile lines, the size, shape and coloring of the teeth and the occlusal plane of the patient precisely and quickly without the need of multiple tools.

These and other features of the present invention will be evident from the ensuing detailed description of preferred embodiments, from the drawings and from the claims.

DETAILED DESCRIPTION OF PREFERRED EMBODIMENTS

The present invention provides a combination tool for measuring anatomical features of a patient for the fabrication of denture bases. Descriptive embodiments are provided before for explanatory purposes. It is to be expressly understood that the present invention is not be limited to these descriptive embodiments. Other embodiments are considered to be within the scope of the present invention, including without limitation the use of the present invention for other applications, such as denture duplication, dental implants, and other dental applications. The descriptions below discuss the systems of the present invention as used in dental labs, but it is to be expressly understood that these systems could also be implemented in the dentist office or through a network allowing interaction between the dentist and the dental lab through the systems. The processes and systems of the present invention may also be used in combination with all or parts of the following co pending applications filed on Nov. 3, 2010, entitled System and Processes for Anatomical Features in Dentures, Ser. No. 12/939,138; System and Process for Duplication of Dentures, Ser. No. 12/939,136; System and Processes for Optimization of Dentures, Ser. No. 12/939,141; and Removable Tool for Denture Uses, Ser. No. 12/939,143; all of which are hereby incorporated herein by reference.

A tool 10 of a preferred embodiment of the present invention is illustrated in FIGS. 1-15. The tool includes several features, including without limitation an impression tray, vertical height measuring mechanism, lip support, occlusal plane plate, a measurement grid for measuring the smile and midline and tooth template and other features critical for defining and measuring anatomical features of a patient for the manufacture of a denture.

The tool 10 includes an upper tray 20 and lower tray 30. The upper tray 20 and lower tray 30 are filled with impressionable material for making an impression of the mandibular and maxilla ridge of the patient. This creates a double arch impression of the patient. A removable handle, as discussed in greater detail below, can be used to remove the trays and impression from the mouth of the patient.

Figure 5:
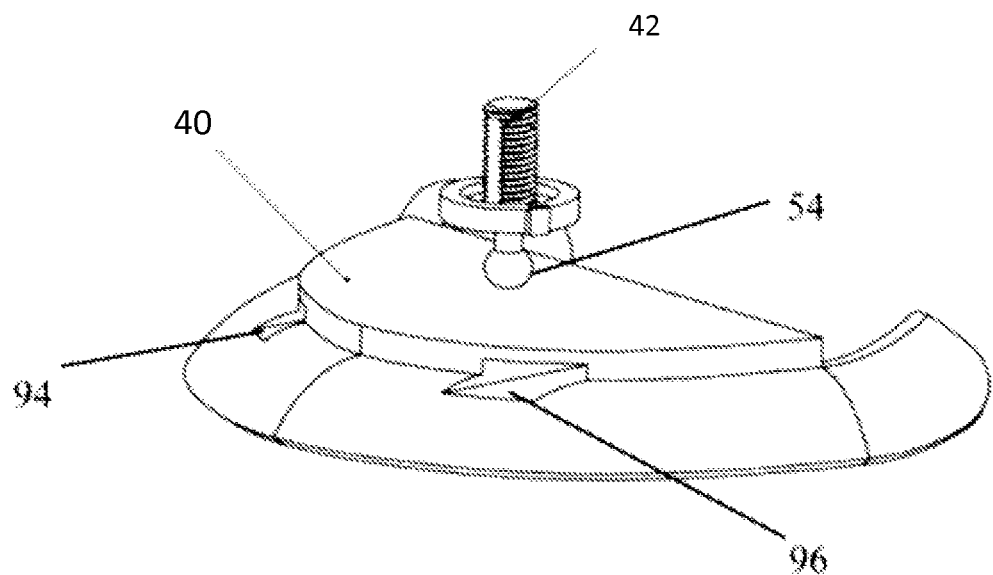
FIG. 5 is a side view of the lower tray of the tool of FIG. 1.
Figure 6:
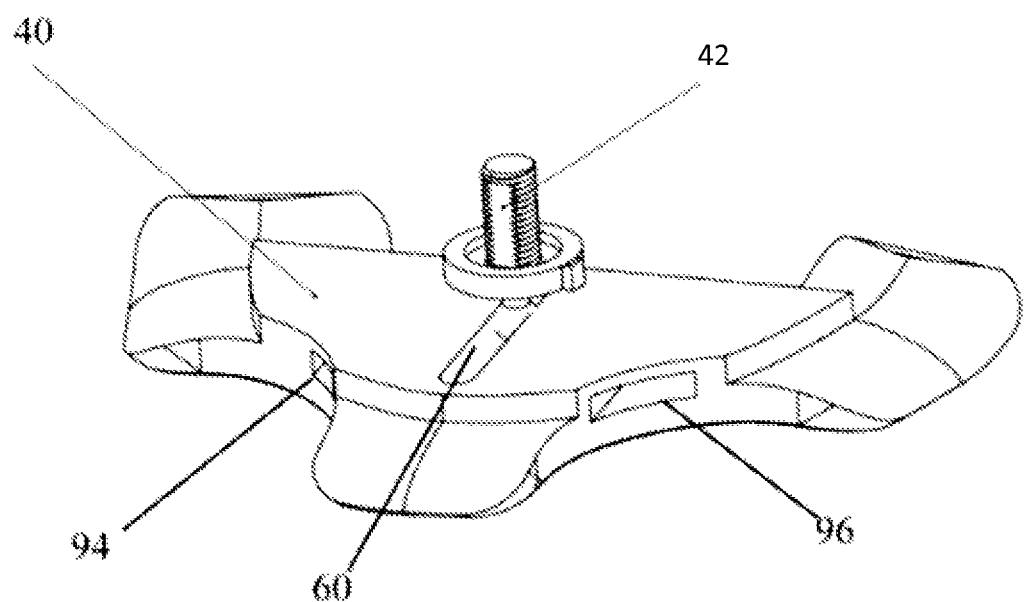
FIG. 6 is a front view of the lower tray of the tool of FIG. 1.
Figure 7:
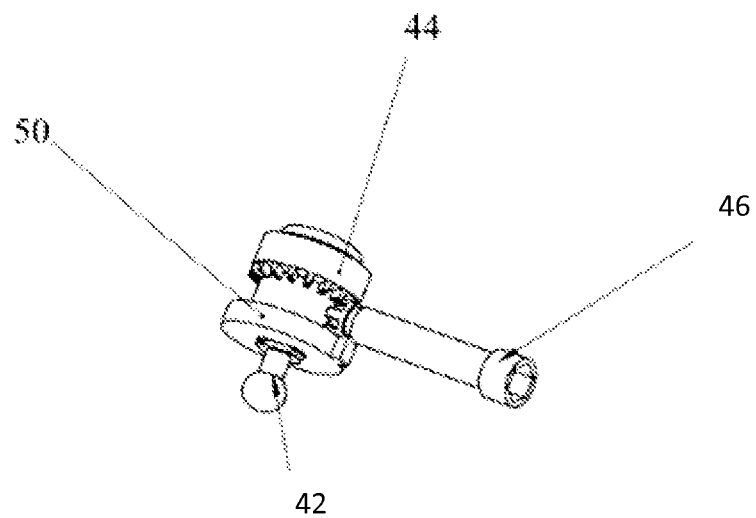
FIG. 7 is a perspective view of the vertical adjustment mechanism of the tool of FIG. 1.
Figure 8:
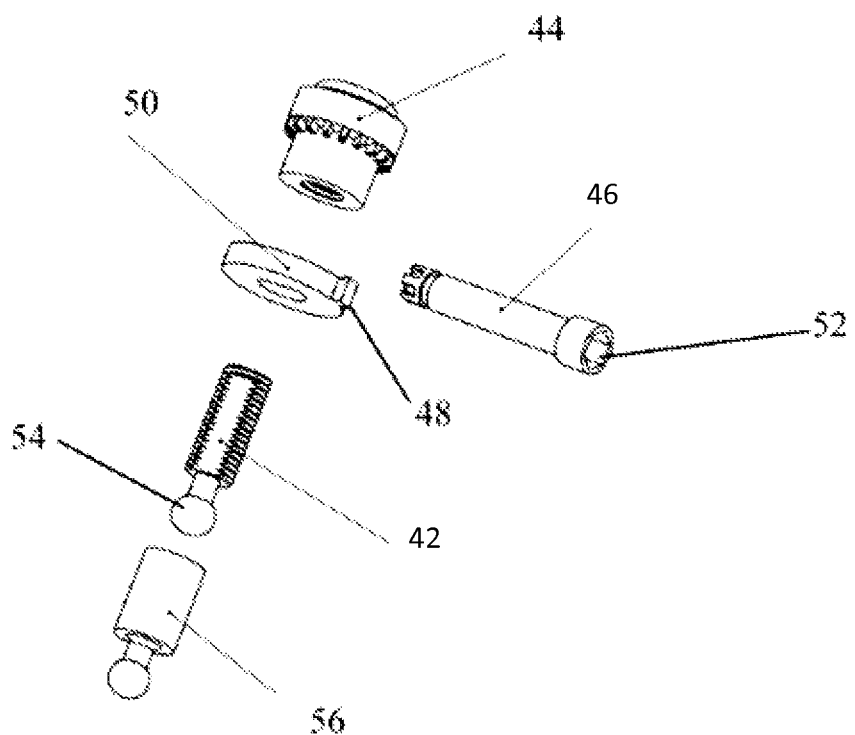
FIG. 8 is an exploded view of the vertical adjustment mechanism of the tool of FIG. 1.

The tool 10 also includes a drive mechanism 40 for adjusting the vertical height of the upper tray 20 and the lower tray 30. This not only assists in creating the impression of the mandibular and maxilla ridge of the patient, but more importantly it allows for precise measurement of the vertical distance between the mandibular and maxilla ridges of the patient. The drive mechanism 40 of a preferred embodiment is illustrated in FIGS. 1-5. The drive mechanism includes threaded bolt 42 that is mounted in thread engagement to drive gear 44. Drive shaft 46 engages in a rack and pinion gear engagement with drive gear 44 and is retained by key 48 on support 50. The drive shaft 46 includes an internal hex socket 52. The support 50 includes an oval inner hole having substantially flattened surfaces that engage the flattened surfaces on the sides of the threaded bolt 42 to prevent rotation of the threaded bolt. A hex tool (not shown) engages in the hex socket 52 to rotate drive shaft 46. The rotation of the drive shaft 46 causes drive gear 44 to rotate which in turn causes vertical movement of the threaded bolt 42. Spherical end 54 engages in a slot 60 on the lower tray 30 as shown in FIG. 5. An extension 56 may also be added to the end of threaded bolt 42 to provide additional vertical extension.

Figure 1:
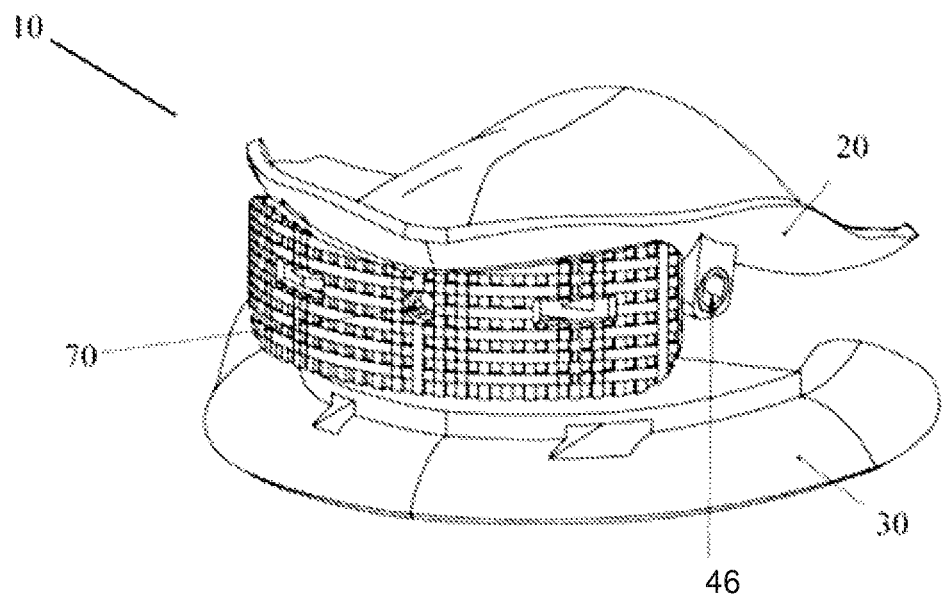
FIG. 1 is a perspective illustration of a preferred embodiment of the tool of the present invention.
Figure 2:
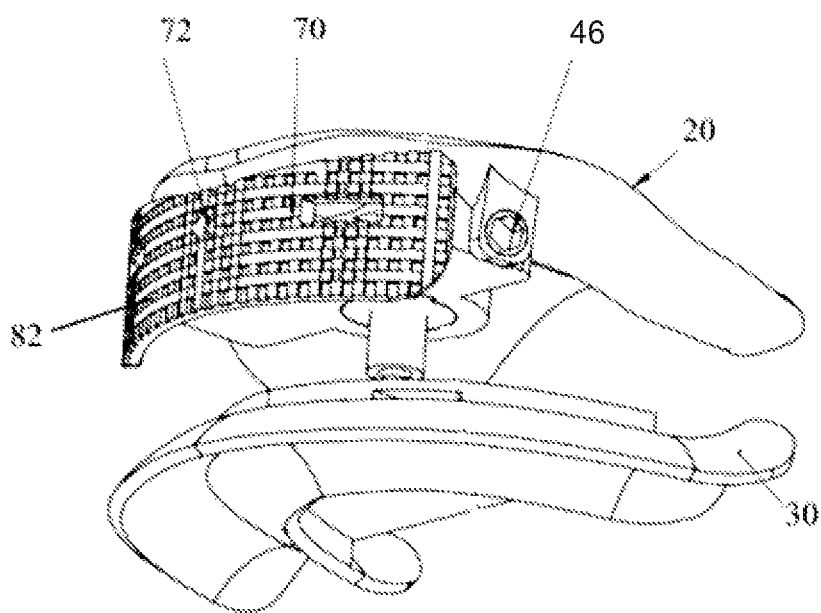
FIG. 2 a lower perspective illustration of the tool of FIG. 1.
Figure 3:
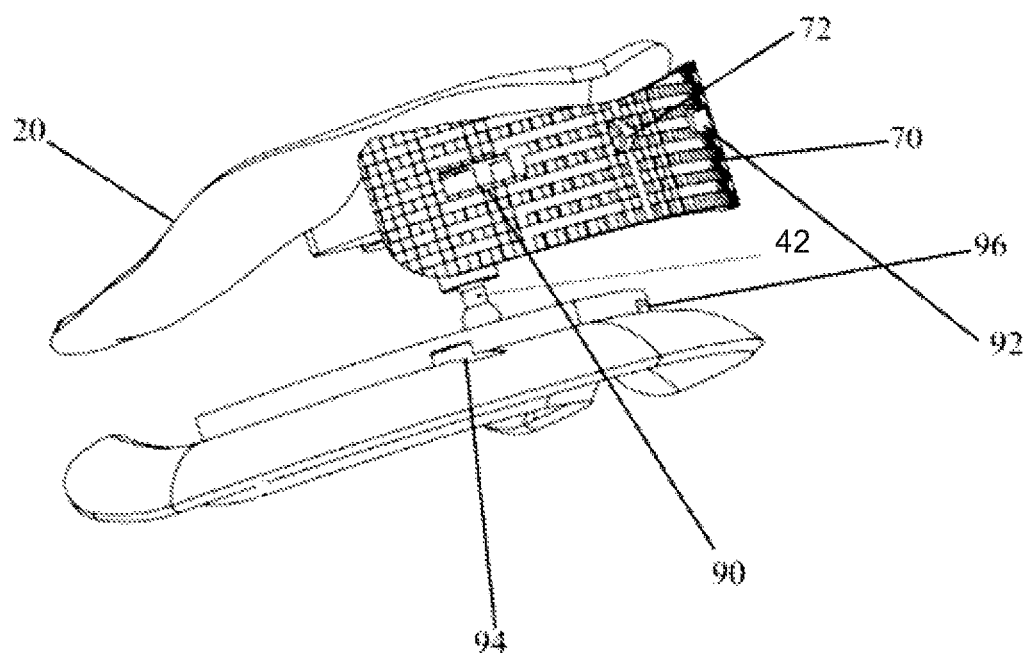
FIG. 3 is a side perspective illustration of the tool of FIG. 1.
Figure 4:
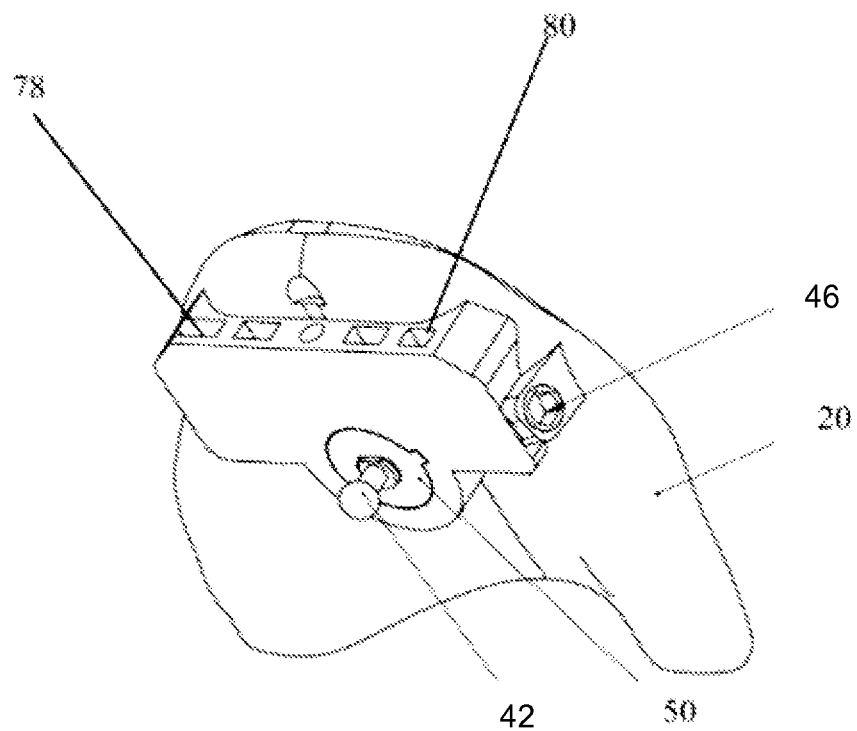
FIG. 4 is a lower perspective view of the upper tray of the tool of FIG. 1.
Figure 9:
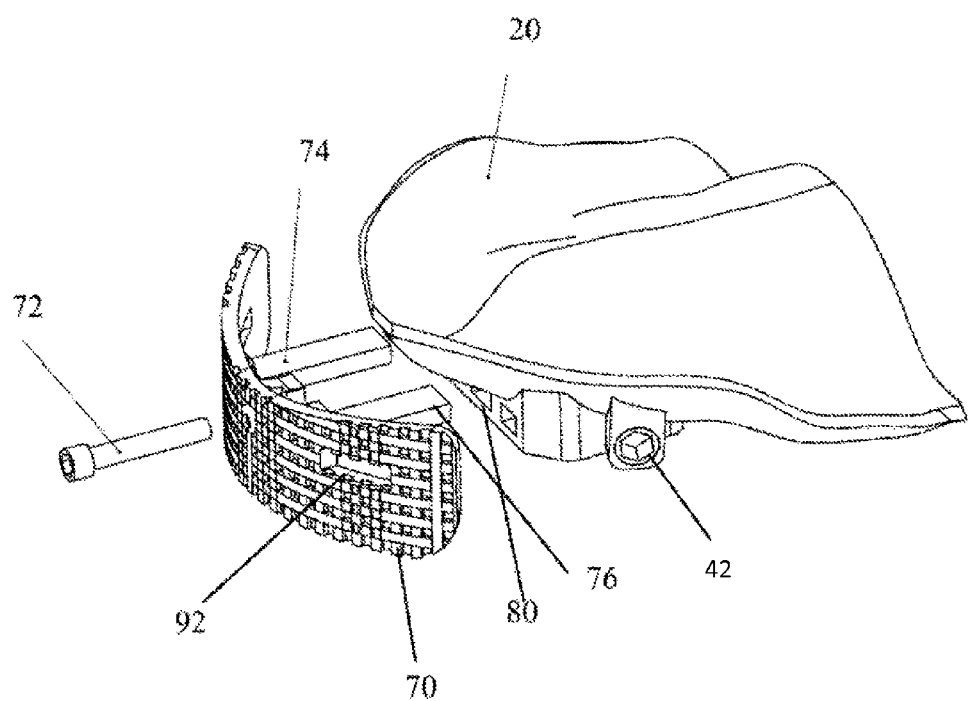
FIG. 9 is a rear view of the lip support of the tool of FIG. 1.
Figure 10:
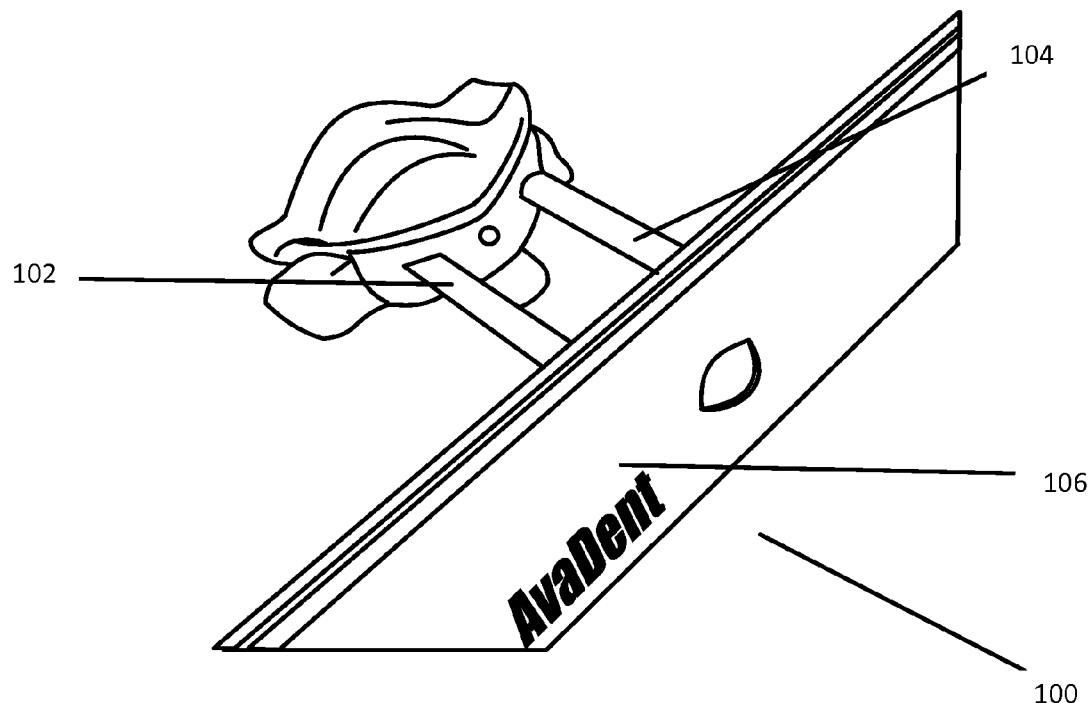
FIG. 10 is a perspective view of the occlusal plane plate component of the tool of FIG. 1.
Figure 11:
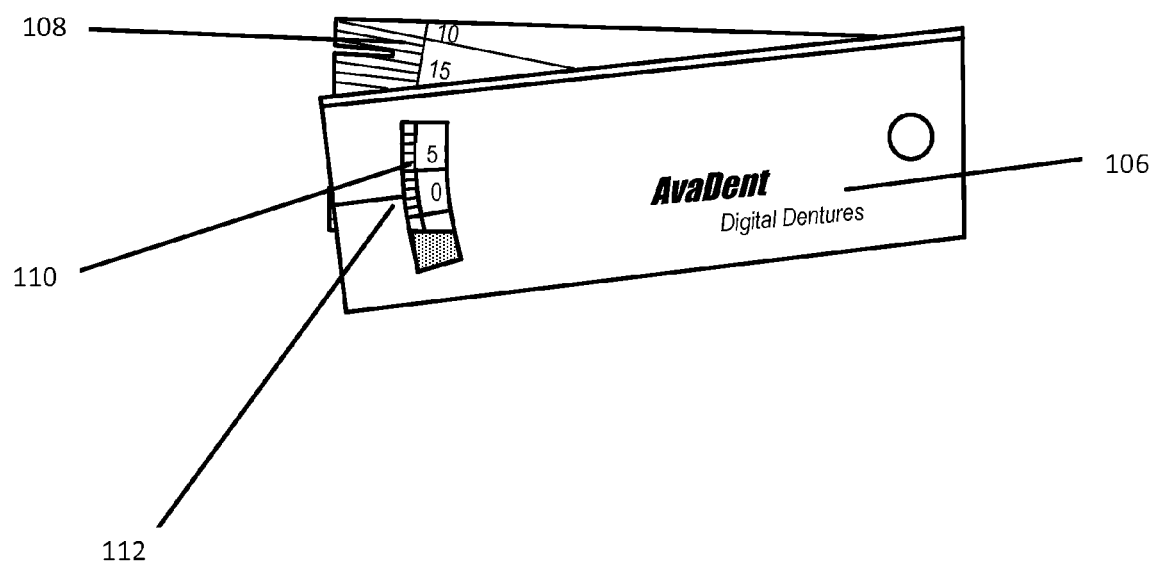
FIG. 11 is a front view of the occlusal plane plate of the tool of FIG. 1.
Figure 12:
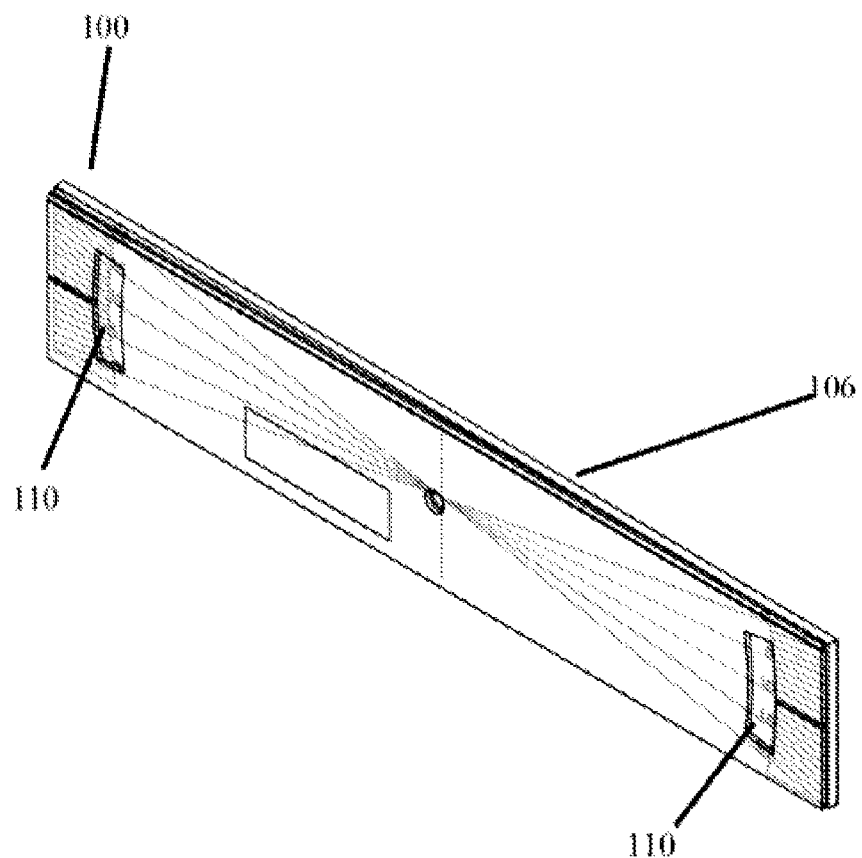
FIG. 12 is a perspective view of the occlusal plane plate tool.
Figure 13:
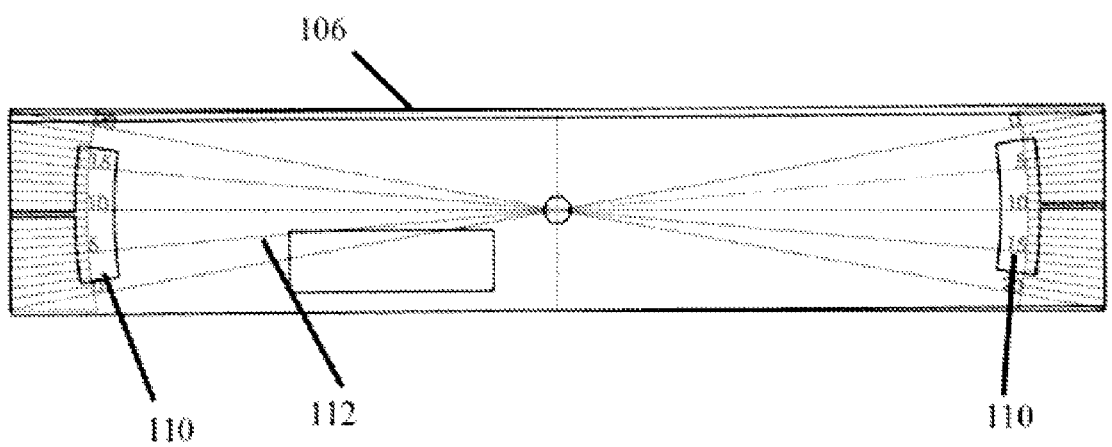
FIG. 13 is a front view of the occlusal plane plate tool.
Figure 14:
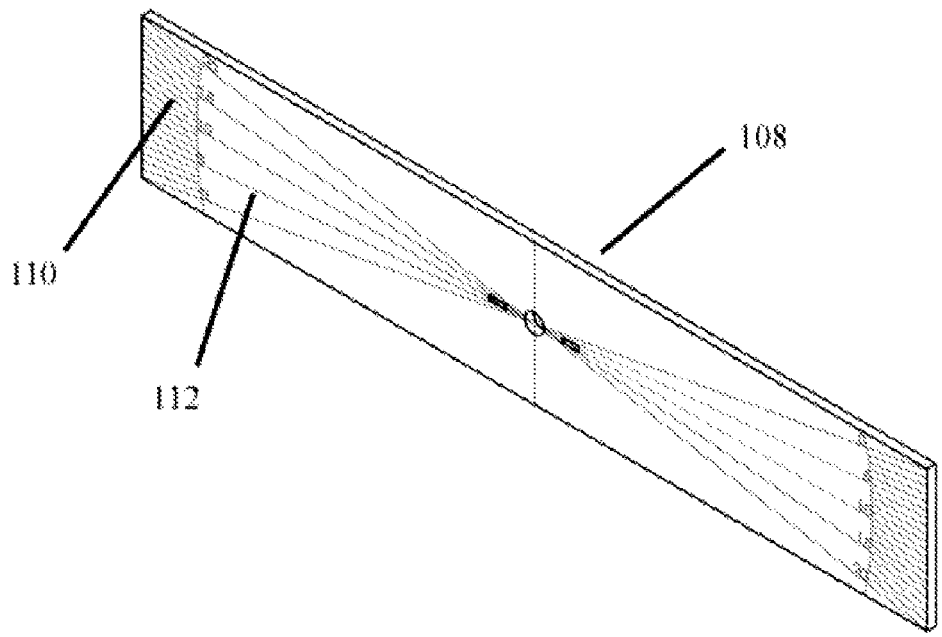
FIG. 14 is a perspective view of the scalar member of the occlusal plane plate tool.
Figure 15:
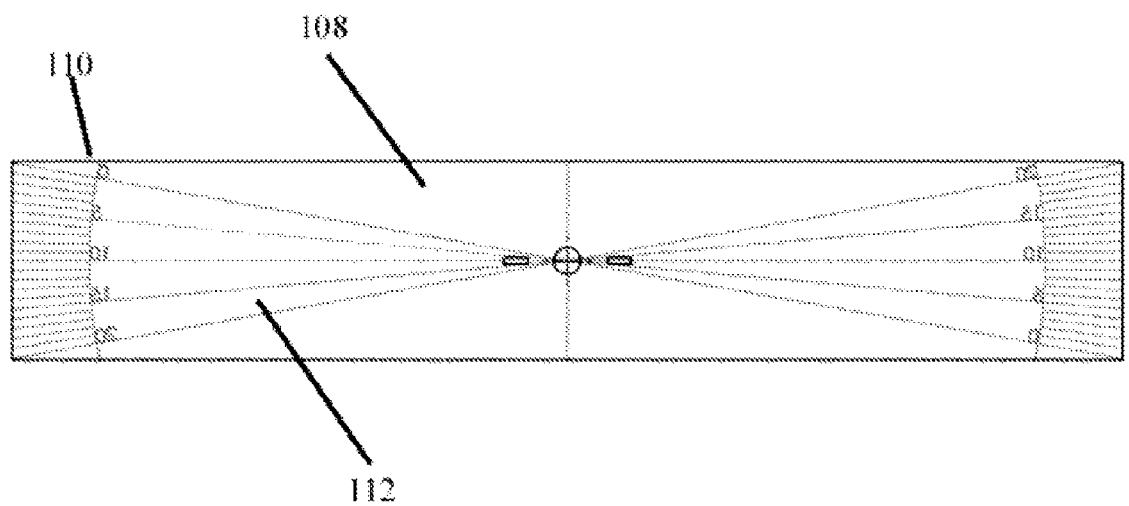
FIG. 15 is a front view of the scalar member.
Figure 16:
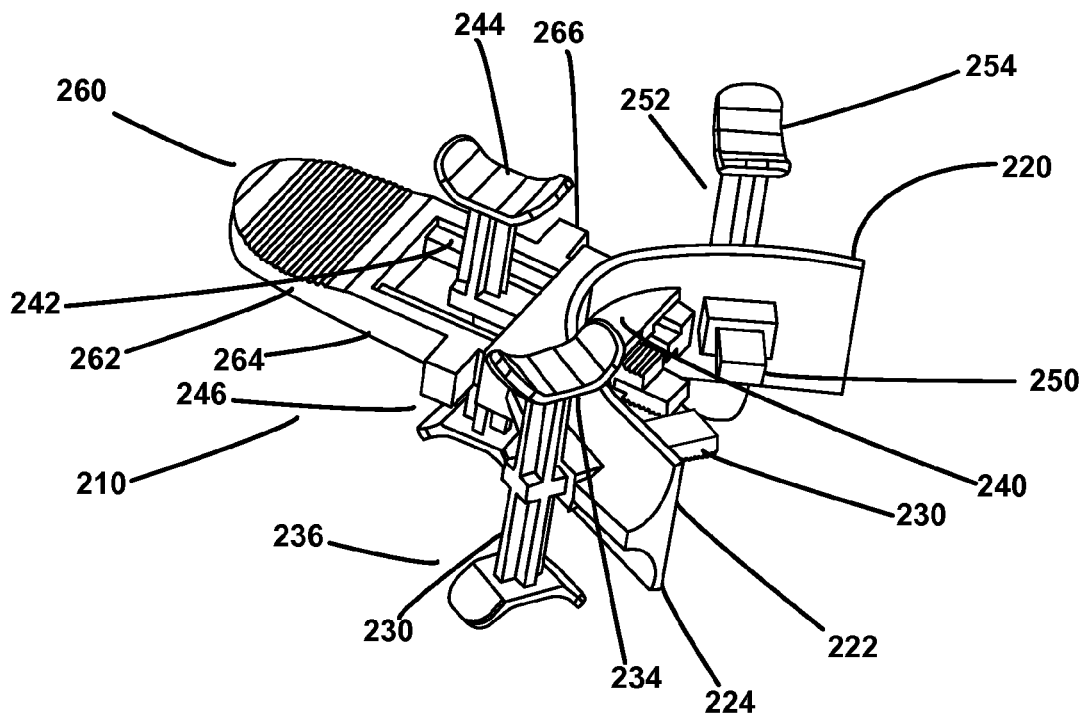
FIG. 16 is an illustration of the tool of another preferred embodiment of the present invention configured for use to be used as a triple tray for double arch registration.
Figure 17:
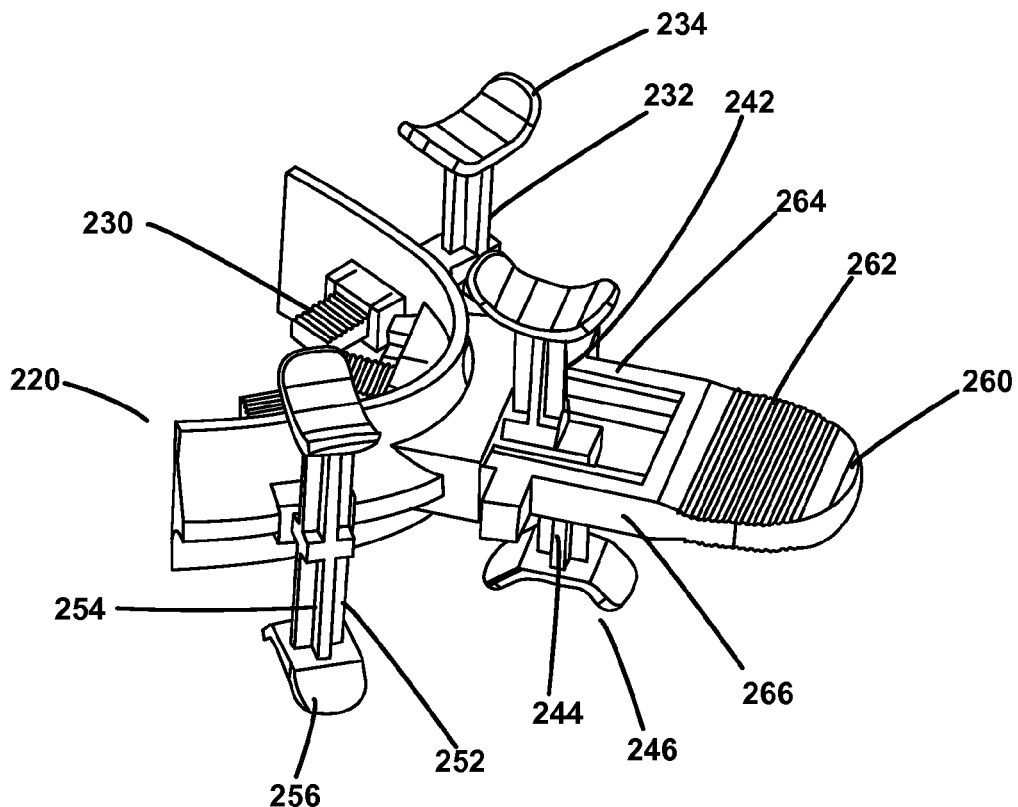
FIG. 17 is an illustration of an opposing perspective view of the tool of FIG. 16.
Figure 18:
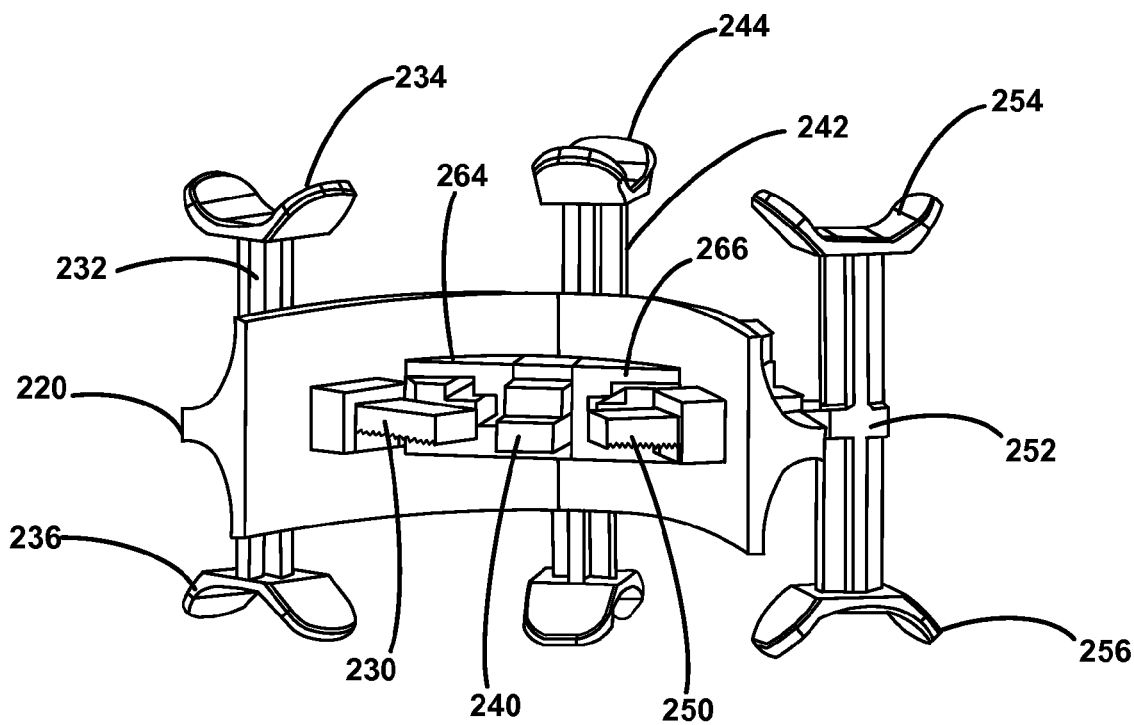
FIG. 18 is an illustration of a rear view of the tool configured in FIG. 16.
Figure 19:
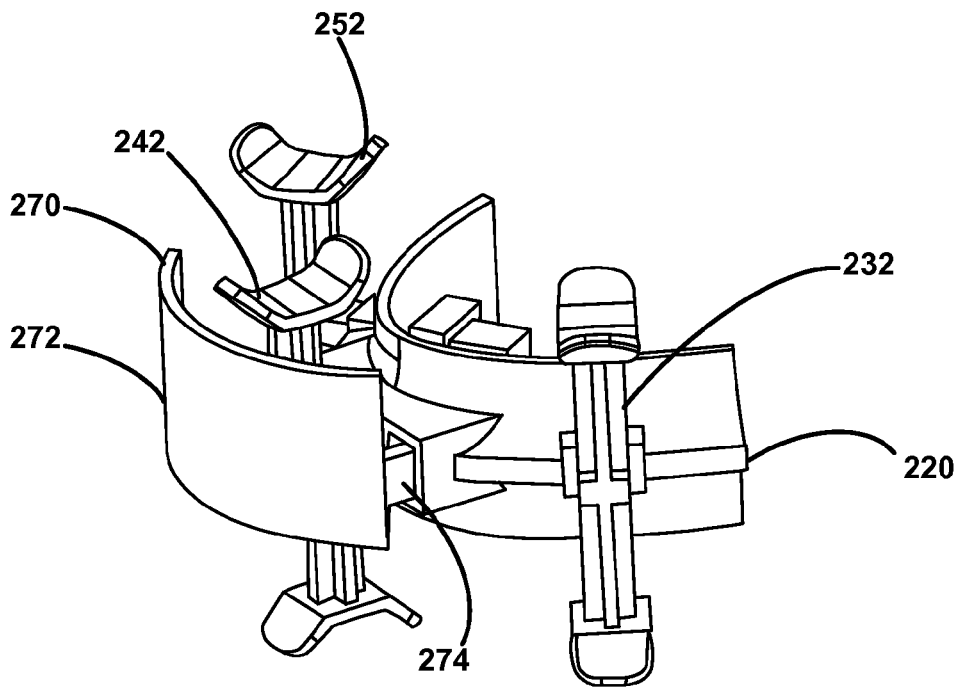
FIG. 19 is an illustration of the tool configured for lip line measurements and for vertical dimensional measurements.

The tool 10 also includes lip support 70 as shown in FIGS. 1, 2 and 9. The lip support 70 is mounted to the upper tray 20 by adjustment bold 72. Horizontal guides 74, 76 engage in guide holes 78, 80 on the upper tray 20. The position of the lip support 70 can be precisely adjustment by the adjustment bold 72. A measurement grid 82 is formed on the outer surface of the lip support 70 to enable precise definition and measurement of the smile line and the mid-line In the preferred embodiment, the grid is in one millimeter increments. The lip support 70 also provides retention for securing teeth templates to the lip support to enable the size, shape and coloring of the patient's teeth to be determined for fabrication of a denture. The lip support 70 can also include additional structure to create additional support for other anatomical features, such as protuberances for the canine teeth, and other such features.

Figure 25:
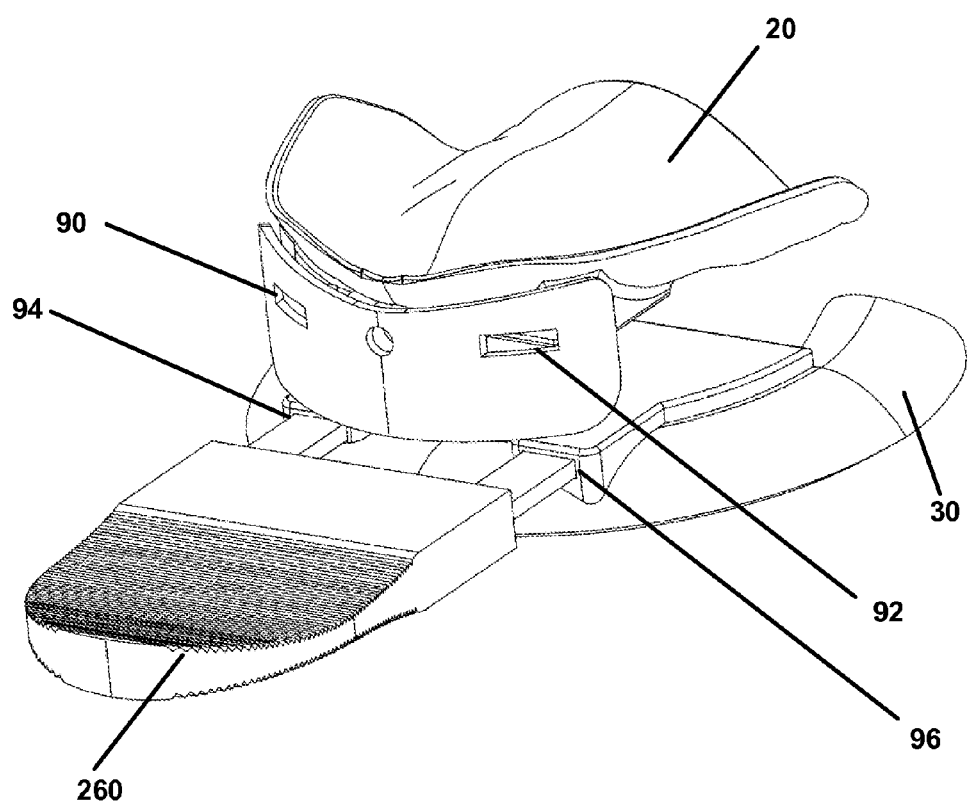
FIG. 25-26 are illustrations of various aspects of the tool of FIG. 1 having a handle.
Figure 26:
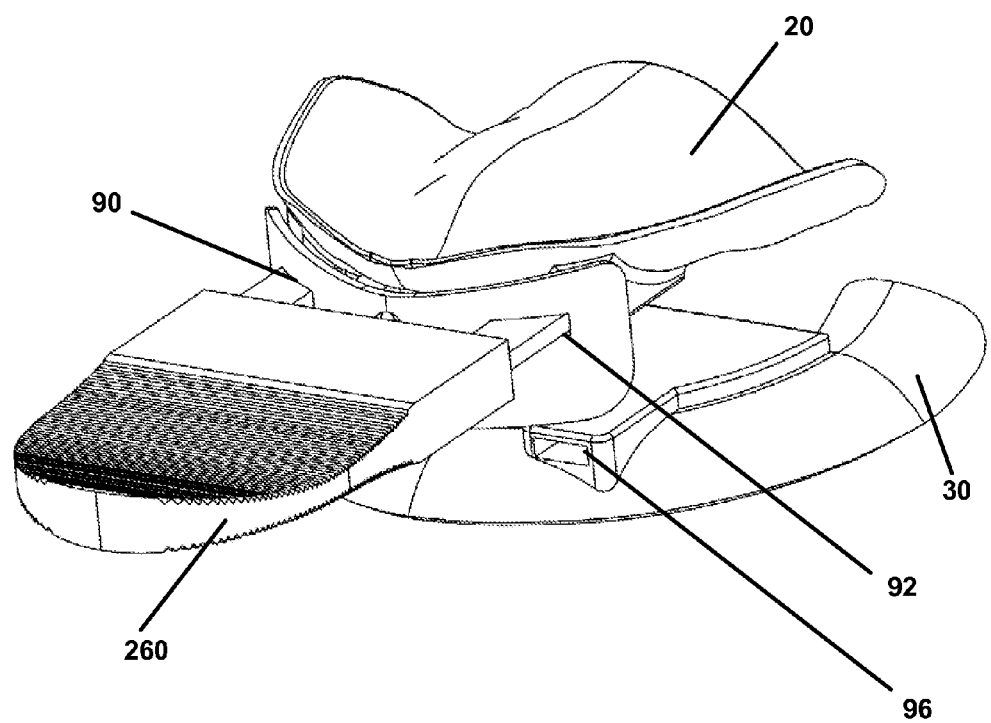

With reference to FIGS. 25 and 26, slots 90, 92 formed in the lip support and slots 94, 96 in the lower tray serve several functions. One function is to provide for engagement with a removable handle 260. This removable handle allows the tool to be easily inserted into the patient's mouth, then removed to allow the appropriate measurements to be made. A second function is to provide a precise alignment with the occlusal plane plate discussed below.

The occlusal plane plate 100, shown in FIGS. 10-14 includes alignment guides 102, 104 that are inserted into slots 94, 96 on the lower tray 30 or slots 90, 92 on the lip support 70. This aligns the occlusal plane plate with the tool 10. The occlusal plane plate 100 includes an elongated rectangular member 106 that is mounted on a perpendicular transverse axis to the tool 10. An inner member 108 having an angular graduated scale 110 is mounted within the member 106 and is pivotal relative to the member 106. The angle of the pivoting movement can be measured by the scale 110 relative to the pointer 112 on the outer member 106. This feature is used to measure the angle of the occlusal plane of the patient relative to the position of the tray in the patient's mouth.

Use

The tool as described above can be used to take the critical measurements of the patient's anatomy for the fabrication of dentures and other denture orthosis. The tool can be initially configured for taking the vertical dimension measurement. The dentist inserts the tool 10 into the patient's mouth. The vertical spacing of the upper and lower trays is adjusted by rotating the drive shaft 46 until the appropriate measurement is taken. Once the vertical dimension has been measured, the upper and lower trays are adjusted to the correct position in the patient's mouth and impression compound is injected to lock the upper and lower tray and the patient's ridges in a fixed vertical position and centric relation. The tool in this configuration is acting as a centric relation tray to obtain a double arch registration. Once the impression has been taken, the handle can be removed and the lip support member can be inserted in lieu thereof. The lip support is carefully inserted into the appropriate position between the lip and gum of the patient. The lip lines of the lip support, mid line and smile lines can be thus measured against the measurement grid. The lip support member is then removed and the occlusal plane plate is inserted in lieu thereof. The reference angle of the occlusal plane relative to the Camper's line can then be measured relative to the occlusal of the incisors and posterior teeth.

Alternative Embodiments

The tool 210 includes mouth base support 220 as shown in FIGS. 16-24. The base support 220 includes an upper ridge support 222 and a lower ridge support 224. Horizontally slidable wing supports 230, 240, 250 are provided to be adjustable depending on the size of the patient's mouth. Vertical height calipers 232, 242, 252 extending from the wing supports with upper curved brackets 234, 244, 254 and lower curved brackets 236, 246, 256. Handle 260 is removably inserted into the center of the base support. Engagement members 264, 266 secure the handle 260 to the base support.

The tool in this configuration is used as a centric relationship tray to take a double arch registration to record vertical and centric jaw registration. The interior of the tray is filled with impression compound and inserted into the mouth. The patient bites down on the impression compound to form the double arch registration. Impression compound can be added when the tray is in the patients mouth. Once the compound has set, the tray is removed by grasping the handle and pulling the tool out.

The vertical height calipers 232, 242, 252 are used to measure the vertical dimension of occlusion, that is the vertical dimension of the face with the posterior teeth fitting together and at rest. The dentist selects the appropriate size of caliper from a variety of calipers that best fits the size of the patient's face. The calipers can be moved horizontally to fit the arch as well as vertically to take the vertical measurements.

Figure 20:
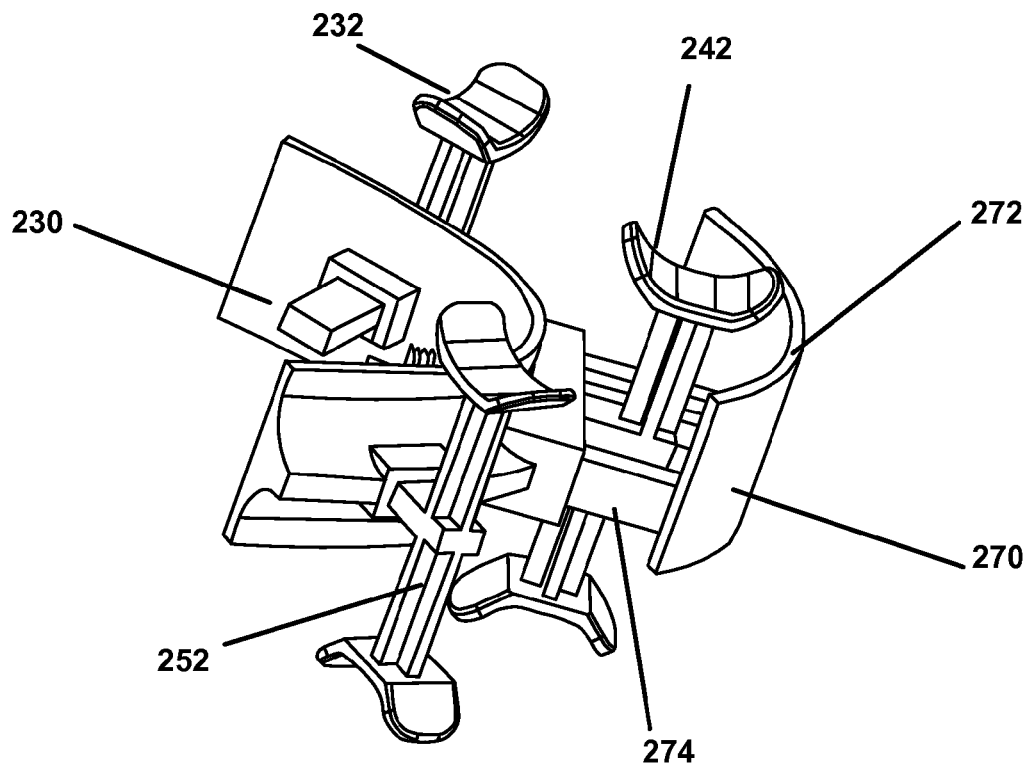
FIG. 20 is an illustration of an opposing perspective view of the tool configured in FIG. 19.
Figure 21:
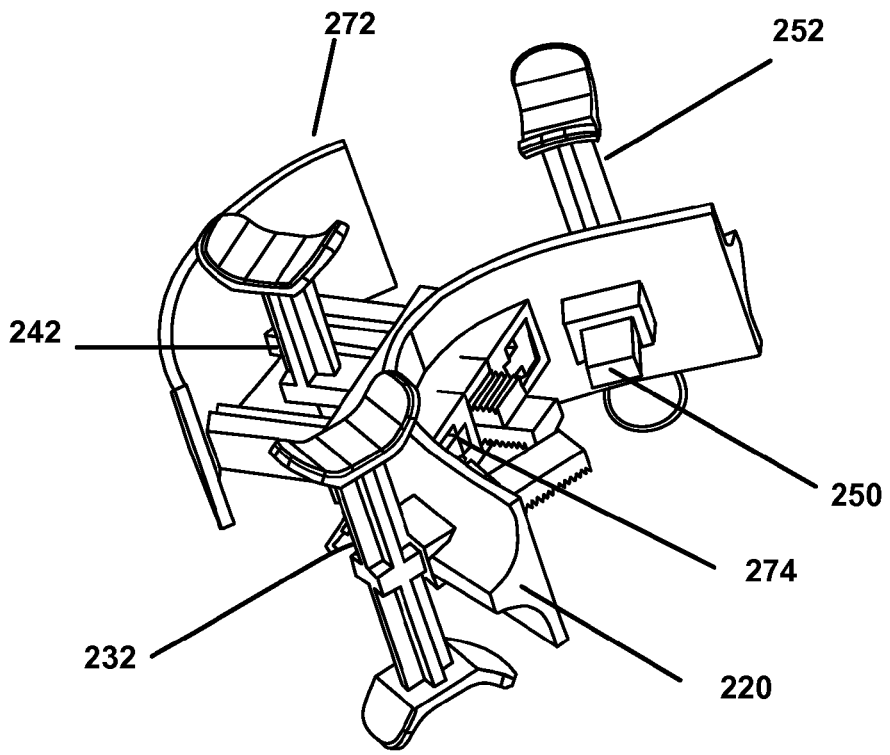
FIG. 21 is an illustration of a rear perspective view of the tool configured in FIG. 19.
Figure 22:
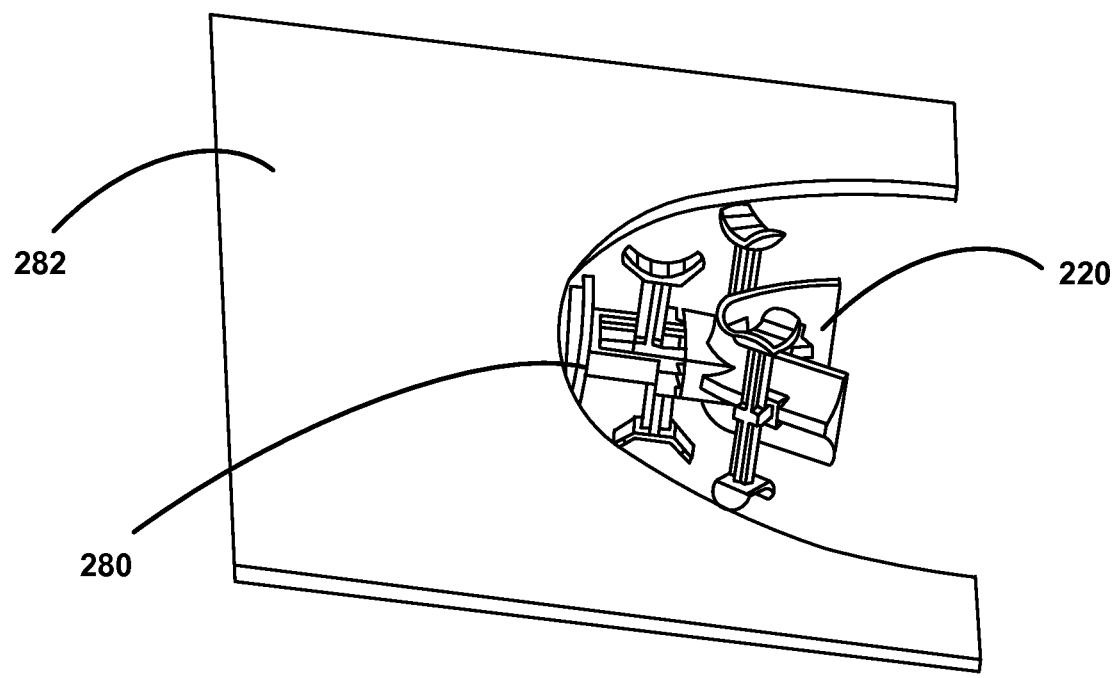
FIG. 22 is an illustration of the tool configured for occlusal plane measurement.

Another embodiment of the tool in a preferred embodiment is illustrated in FIGS. 20-22. In this embodiment, the handle 260 is removed from the base support by disengaging the members 262, 264 from base support. In this embodiment, lip support 270 is inserted by slider 274 in lieu of the handles. The lip support includes a vestibule shield 272. The vestibule shield includes a vertically extending measurement scale.

The tool is then inserted into the mouth so that the lip extends over the vestibule shield. The handle can be removed to allow measurements of the lips and vertical height to be taken.

Figure 23:
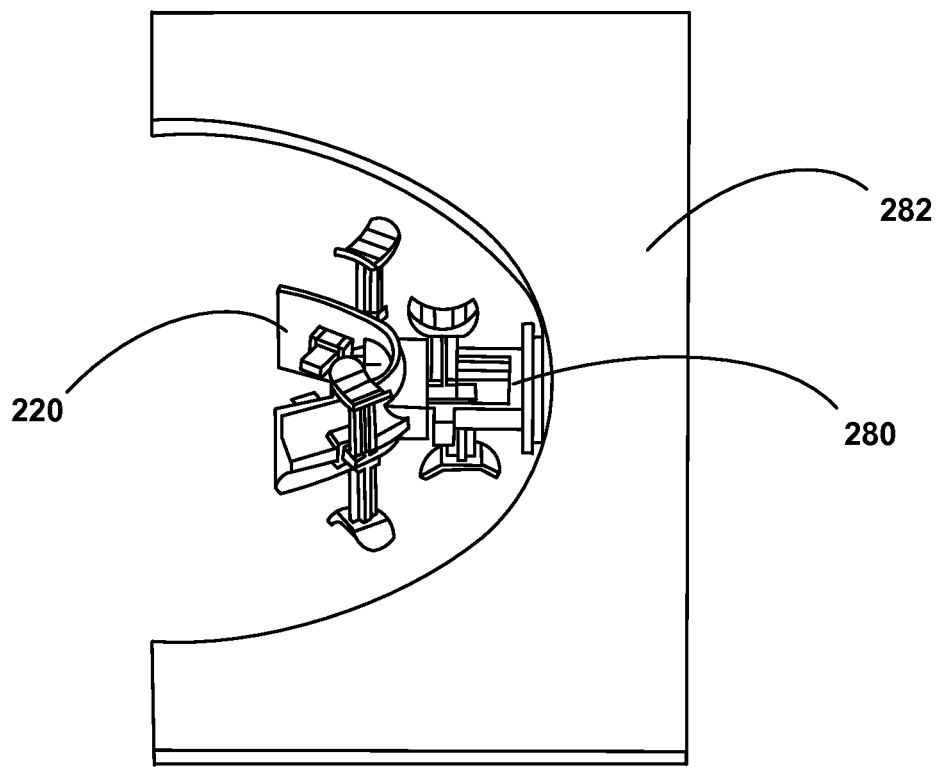
FIG. 23 is an illustration of an opposing perspective view of the tool configured in FIG. 18.
Figure 24:
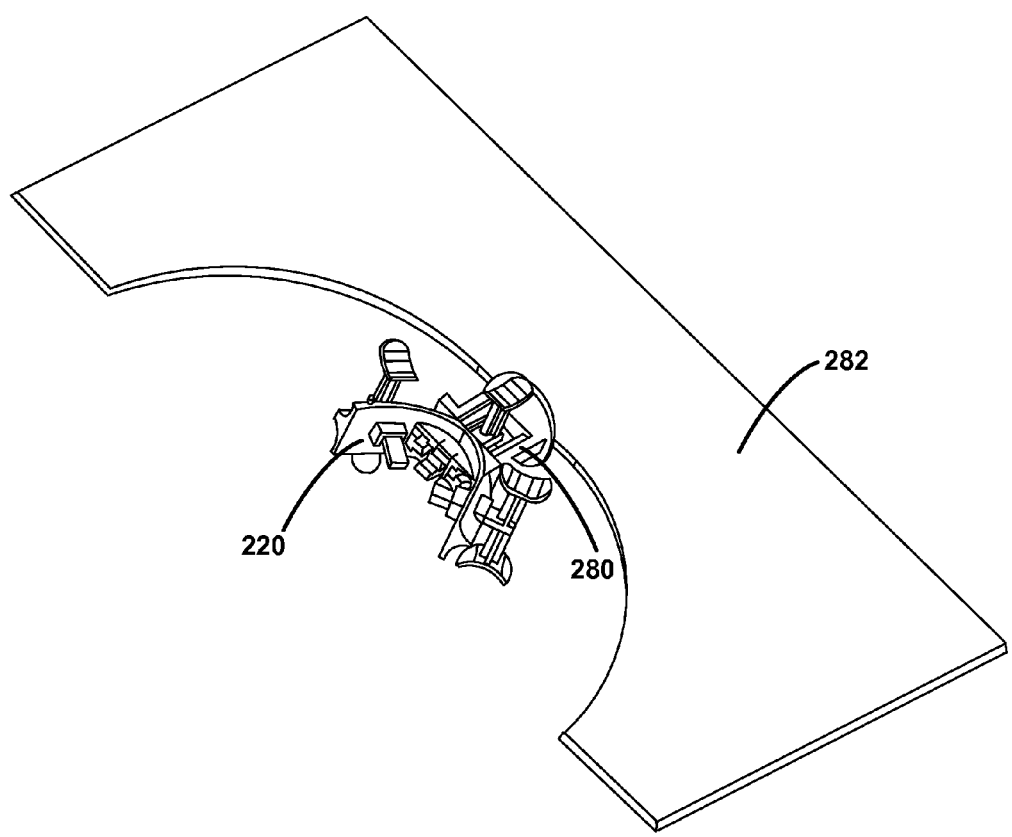
FIG. 24 is an illustration of a rear perspective view of the tool configured in FIG. 18.

A third configuration of the tool 210 is illustrated in FIGS. 22-24. The handle and lip supports are removed from the base support and the occlusal plane member 280 is inserted into the base support. The occlusal plane member 280 includes a flat planar surface member 282 extending from a cut-out portion 284 that will extend around the face and head of the individual being measured. The base support is inserted into the mouth, and the occlusal plane can be determined by registering the planar member 282 which should coincide with a horizontal plane that touches the incisal edges of the incisors and tips of the occluding surface of the posterior teeth. A normal occlusal plane extends parallel to a line drawn from the tragus of the ear to the ala of the nose and parallel to the interpupillary line (Camper's Line). The tool is inserted in the mouth, the patient bites down so vertical height set by the tray. The planar member 282 will be adjusted. The occlusal plane member can then be compared to the normal occlusal plane. Deviations from the norm can then be compensated in the new dentures.

Use

The tool as described above can be used to take the critical measurements of the patient's anatomy for the fabrication of dentures and other denture orthosis. The tool can be initially configured for taking the vertical dimension measurement. The dentist selects the calipers appropriate for the size of the patient's face. The calipers are adjusted horizontally and vertically to the desired position relative to the patient's face. Once the vertical dimension has been measured, the horizontal wing supports are fixed to the correct position in the patient's mouth and impression compound is injected. The tool in this configuration is acting as a centric relation tray to obtain a double arch registration. Once the impression has been taken, the handle can be be removed and the lip support member can be inserted in lieu thereof. The vestibule shield is carefully inserted into the appropriate position between the lip and gum of the patient. The lip lines of the lip support, mid line and smile lines can be thus measured. The lip support member is then removed and the occlusal plane member is inserted in lieu thereof. The reference angle of the occlusal plane relative to the Camper's line can then be measured relative to the occlusal of the incisors and posterior teeth.

The above described embodiments are provided for explanatory purposes and are not meant to limit the scope of the inventions.

What is claimed is:

1. A tool for measuring anatomical features for the manufacture of dentures, said tool comprising:
   a lower tray for creating an impression of a lower arch;
   an upper tray for creating an impression of an upper arch;
   a plurality of guide holes comprising apertures in the lower tray, and the upper tray;
   an adjustment mechanism for adjusting the vertical spacing between said lower tray and upper tray;
   a detachable lip support for detachable engagement with said upper tray comprising:
      a plurality of horizontal guides engagable in the guide holes comprising apertures in the upper tray; and
      a plurality of lip support guide slots;
   a removable occlusal plane plate whereby the occlusal plane of the patient is determinable; and
   an attachment mechanism for detachably securing said removable occlusal plane plate by alignment guides insertable in at least one of:
      the guide holes comprising apertures in the lower tray, and the lip support guide slots;
a removable handle insertable in:
    the guide holes comprising apertures in the lower tray, and
    the plurality of lip support guide slots.

2. The tool of claim 1 wherein said lip support further includes:
    a horizontal adjustment mechanism to adjust the spacing of said lip support relative to the upper tray.

3. The tool of claim 1 wherein said lip support further includes:
    a horizontal adjustment mechanism to adjust the spacing of said lip support relative to the upper tray; and
    said horizontal adjustment mechanism includes a bolt for adjusting the horizontal spacing.

4. The tool of claim 1 wherein said lip support further includes:
    a measurement grid for defining and measuring the lip lines, smile lines and mid lines of the patient.

5. The tool of claim 1 wherein said lip support further includes:
    a template attachment mechanism for attaching a template for determining the size, shape and coloring of the teeth of the patient.

6. A method for defining and measuring anatomical features of a patient for the fabrication of a denture using a single tool having an upper tray, lower tray, vertical adjustment mechanism between said upper and lower trays, a removable lip support and a occlusal plane plate component, wherein said method includes the steps of:
    inserting the upper and lower trays in the mouth of the patient wherein the upper tray and the lower tray are filled with impressionable material for making an impression of at least one of the mandibular and maxillar ridges of the patient;
    adjusting the vertical spacing with the vertical adjustment mechanism of the upper and lower trays to determine the vertical measurement of the patient;
    forming an impression of at least one of the mandibular and maxillar ridges of the patient;
    inserting adhesive compound between the upper and lower trays to lock the upper and lower trays to each other and to fix the vertical height and centric relation of the upper and lower trays;
    removing the impression by inserting a removable handle in the upper or lower tray;
    reinserting the upper and lower trays in the mouth of the patient;
    attaching the lip support to the upper or lower tray;
    measuring the lip lines, mid lines and smile lines of the patient from a measurement grid on the lip support;
    attaching a template to the lip support to determine the size, shape and coloring of teeth; and
    attaching the occlusal plane plate to the lip support or upper or lower tray to determine the occlusal plane of the patient.

7. The method of claim 6 wherein said step of attaching the lip support to the tool includes:
    adjusting the spacing of the lip support relative to the upper and lower trays.

8. A tool for measuring anatomical features for the manufacture of dentures, said tool comprising:
    a lower tray for creating an impression of a lower arch;
    an upper tray for creating an impression of an upper arch;
    an adjustment mechanism for adjusting the vertical spacing between the lower tray and upper tray;
    a lip support for engagement on one of the upper tray and lower tray;
    an occlusal plane plate comprising:
        an elongated rectangular member comprising a window and a pointer whereby an angle of the elongated rectangular member may be determined;
        an inner member having an angular graduated scale viewable through the window,
            wherein the elongated rectangular member is pivotable with respect to the angular graduated scale of the inner member,
            whereby the elongated rectangular member is alignable with the incisal edges of the incisors and tips of the occluding surface of the posterior teeth, and
            whereby the angle of the patient's dentition relative to the position of the tool may be measured by comparing the pointer to the angular graduated scale,
    alignment guides for positioning the inner member in relation to the lip support or upper or lower tray, wherein the inner member is fixed in relation to the alignment guides; and an attachment mechanism for securing the occlusal plane plate to the lip support or upper or lower tray.

* * * * *